United States Patent
Gagel et al.

(10) Patent No.: US 8,430,833 B2
(45) Date of Patent: Apr. 30, 2013

(54) DEVICE AND METHOD FOR TRANSPORTING MEDICINAL LIQUIDS

(75) Inventors: Alfred Gagel, Litzendorf (DE); Peter Imhof, Bergrheinfeld (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 925 days.

(21) Appl. No.: 11/921,029

(22) PCT Filed: May 26, 2006

(86) PCT No.: PCT/EP2006/005080
§ 371 (c)(1),
(2), (4) Date: Nov. 26, 2007

(87) PCT Pub. No.: WO2006/125671
PCT Pub. Date: Nov. 30, 2006

(65) Prior Publication Data
US 2009/0043239 A1    Feb. 12, 2009

(30) Foreign Application Priority Data
May 27, 2005 (DE) .......................... 10 2005 024 363

(51) Int. Cl.
*A61M 37/00* (2006.01)

(52) U.S. Cl.
USPC ........................................ 604/6.11; 604/6.01

(58) Field of Classification Search ........ 604/4.01–6.16, 604/27, 29–33, 131, 151; 417/44.1, 413.1, 417/415, 44.9
See application file for complete search history.

(56) References Cited

U.S. PATENT DOCUMENTS

| | | | |
|---|---|---|---|
| 3,812,843 A | | 5/1974 | Wootten et al. |
| 4,770,769 A | | 9/1988 | Schael |
| 5,431,634 A | | 7/1995 | Brown |
| 5,722,956 A | * | 3/1998 | Sims et al. ................ 604/131 |
| 6,065,940 A | | 5/2000 | Fleischer et al. |
| 6,254,572 B1 | * | 7/2001 | Knipfer et al. ............. 604/151 |
| 2003/0220609 A1 | | 11/2003 | Childers et al. |
| 2004/0234377 A1 | * | 11/2004 | Bolt ............................. 417/44.1 |
| 2007/0040454 A1 | * | 2/2007 | Freudenberger et al. ..... 310/12 |

FOREIGN PATENT DOCUMENTS

| | | |
|---|---|---|
| DE | 2 410 868 A1 | 9/1974 |
| DE | 28 38 414 A1 | 3/1980 |
| DE | 34 16 057 C2 | 2/1988 |
| DE | 101 08 506 A1 | 8/2002 |
| EP | 0 160 272 A2 | 11/1985 |
| EP | 0160272 A2 * | 11/1985 |
| JP | 61-033666 | 2/1986 |
| JP | 06-002650 | 1/1994 |
| JP | 2001-505978 | 5/2001 |
| JP | 2005-513340 | 5/2005 |
| WO | WO 99/30756 | 6/1999 |
| WO | WO 03/054392 A1 | 7/2003 |

* cited by examiner

*Primary Examiner* — Philip R Wiest
(74) *Attorney, Agent, or Firm* — Jacobson Holman PLLC

(57) ABSTRACT

A device and a method for delivering fluids, preferably for delivering medical fluids, such as in the field of dialysis, include at least one pump designed as a displacement pump and at least one control unit that controls the operation of the pump. The pump is actuated by the control unit such that during a suction stroke in a first operating condition the pump takes in a volume exceeding a desired delivery volume for the purpose of discharging a desired delivery volume, and discharges portions of the volume taken in by performing a plurality of partial delivery strokes in the form of partial volumes which are smaller than the volume taken in.

21 Claims, 3 Drawing Sheets

PRIOR ART

PRIOR ART

DEVICE AND METHOD FOR TRANSPORTING MEDICINAL LIQUIDS

CROSS-REFERENCE TO RELATED APPLICATION

This is a national stage of International Application No. PCT/EP2006/005080 filed on May 26, 2006 and published in Germany.

BACKGROUND OF THE INVENTION

1. Field of Invention

This invention relates to a device for delivering fluids, preferably for delivering medical fluids, comprising at least one pump designed as a displacement pump and at least one control unit controlling the operation of the pump.

2. Description of the Prior Art

The use of displacement pumps is known in many different fields of application, such as in the field of medical engineering. Dialysis machines are known, for instance, in which dialysis fluid is prepared with the aid of displacement pumps. In such dialysis machines, the dialysis fluid is prepared from ultrapure water (RO water) and from one or more concentrates containing the required electrolytes and other constituents. The ultrapure water and the concentrates are mixed in a suitable ratio. The mixing ratio between ultrapure water and concentrate can for instance be about 34:1 or 44:1. Other ratios are of course also conceivable.

The delivery of concentrate frequently is performed by means of diaphragm pumps operating with a defined stroke volume. A dialysis machine with a diaphragm pump for delivering the concentrate is known from DE 28 38 414. In the machine known from this document, ultrapure water is mixed with concentrate upon passing through a pressure-reducing valve. The delivery of the concentrate is effected in synchronism with the actuation of the balancing device, so that per cycle of the balancing device one cycle or a defined number of cycles of the pump is each performed.

In prior art dialysis machines, the dialysis fluid frequently is prepared in discrete portions, i.e. in the form of so-called batches. The quantity of the concentrate to be delivered is not constant, but can vary from concentrate to concentrate or in dependence on the treatment to be performed. Thus, with different concentrates it frequently occurs that the same need not all be delivered in the same quantity, but that the delivery volumes can differ considerably. It is conceivable, for instance, that with a batch volume of 30 ml the range of the delivery volumes extends from 200 µl to 2200 µl.

Displacement pumps involve the problem that the accuracy of the delivery depends on the delivery volume. A particularly high accuracy is obtained when for one batch a stroke with a delivery volume is used, which corresponds to the maximum possible delivery volume per stroke or at least approximately corresponds to the same.

An example of a diaphragm pump known from the prior art is shown in FIG. 2 in a longitudinal section. The pump includes a diaphragm 10, which defines the delivery space of the pump on one side and whose movement leads to a delivery of fluid. The movement of the diaphragm 10 is realized by an eccentric drive 20 with stepper motor. The connecting rod 22 is connected with the diaphragm 10 and translates the movement of the eccentric drive 20 into a movement of the diaphragm 10. Reference numeral 30 designates the pump housing, which is composed of the drive housing and the pump head screwed to the same, which also includes the valves controlling the filling and evacuation of the delivery space. In FIG. 2, one of the valves is designated with the reference numeral 40.

FIG. 1 shows a pump characteristic of the pump shown in FIG. 2. In the embodiment illustrated here, the pump is dimensioned such that it can deliver a maximum of about 1200 µl per stroke. In this pump, the required accuracy of 1% starting with delivery volumes of about 600 µl can easily be realized by an individual calibration of the pump. As regards accuracy, however, the lower range of 200 µl to 600 µl turns out to be more problematic, the range between 200 µl and 300 µl being particularly important for the use of dry concentrate. Due to the dependence on the input and output pressure and on the existing time drift, accuracy neither can be achieved in this range by a better calibration.

This results in the problem that in particular for small delivery volumes special pumps would be required to ensure the required accuracy, which would involve the disadvantage of a comparatively large amount of apparatus.

A dialysis machine with a plurality of concentrate pumps is known for instance from EP 160 272. One of the concentrate pumps is intended to provide a basic dialysis fluid, whose ion concentration is absolutely necessary for the treatment. The second concentrate pump effects the adaptation of the ion concentration of the dialysis fluid to the individual requirements, which can vary from patient to patient.

From WO 99/30756 a displacement pump of a dialysis machine is known, which delivers concentrate from a container to a mixing point. As soon as the filling level in the container falls below a specified level, the container is filled with concentrate beyond the specified level by a delivery pump of the same construction. In this way, it is ensured that upon operation of the pump evacuating the container, there is always emitted a signal, which is generated when the level falls below the specified filling level. The signal activates the pump filling the container.

SUMMARY OF THE INVENTION

It is the object of the present invention to develop a device as mentioned above such that with a small amount of apparatus a precise dosage of the fluid also becomes possible with smaller delivery volumes.

This object is solved by a device with the features described herein. Accordingly, it is provided that the pump can be actuated by a control unit such that during a single suction stroke in a first operating condition the pump sucks in a volume exceeding the desired delivery volume for the purpose of discharging a desired delivery volume and discharges portions of the volume sucked in by performing a plurality of partial delivery strokes in the form of partial volumes which are smaller than the volume sucked in. The invention thus consists in that for delivering a specific volume, a larger volume is sucked in during a suction stroke. Upon suction, this volume preferably is limited by closing the inlet valve. Due to the comparatively large volume sucked in, a high accuracy is obtained. Upon completion of the suction stroke, the volume sucked in is discharged in portions, and preferably it is intended that the partial volumes at least approximately correspond to the desired delivery volumes.

Systematic differences in the partial volumes possibly can be corrected by a pump software. An additional calibration also is conceivable, in order to improve the accuracy of the partial volumes.

It is an essential advantage of the invention that on average the partial volumes are approximated to the desired delivery volumes with a high accuracy or correspond to the same in the ideal case.

Further advantages of the invention are also described herein.

The pump can be any kind of displacement pump, such as a diaphragm or piston pump.

Particularly advantageously, the pump can be actuated by the control unit such that the volume sucked in during a suction stroke, which exceeds the desired delivery volume, lies in a range from 0.5 to 1.0 of the maximum delivery volume per stroke of the pump. As stated above, a particularly high accuracy is obtained when a volume is sucked in which is rather close to the maximum delivery volume. In a further aspect of the invention, it therefore is provided that the pump can be actuated by the control unit such that the volume sucked in during a suction stroke, which exceeds the desired delivery volume, at least approximately corresponds to the maximum delivery volume of the pump.

If identical or substantially identical partial volumes should be provided, as can be the case for instance when the pump is used for delivering concentrate for preparing a dialysis fluid, it can be provided that the pump can be actuated by the control unit such that the partial volumes discharged are identical or substantially identical.

The ratio of the volume sucked in during a suction stroke to the partial volume discharged during each partial stroke can be as desired. In one aspect it is provided that the ratio of the volume sucked in to a partial volume discharged is about 10:1 or below. Thus, it is conceivable for instance that a partial volume amounts to one half or one third of the volume sucked in, i.e. two or three partial delivery strokes are effected before the next suction stroke is performed.

In one embodiment of the invention, the device of the invention always is operated in said first operating condition, in which the volume sucked in during a suction stroke is divided into a plurality of partial volumes. Furthermore, one aspect of the invention is conceivable, in which the pump can be operated in a second operating condition, in which the volume sucked in is not divided into partial volumes, but the volume sucked in during a suction stroke is discharged in one delivery stroke.

It can be provided that the pump can be actuated by the control unit such that the choice of the operating condition by the control unit depends on the desired delivery volume.

As stated above, inaccuracies in the delivery can be obtained in particular when relatively small volumes should be delivered. Therefore, a further aspect of the invention consists in that the pump can be actuated by the control unit such that the first operating condition is set with smaller desired delivery volumes and the second operating condition, in which the volume sucked in is discharged in one delivery stroke, is set with comparatively larger desired delivery volumes.

It is conceivable that the pump can be actuated by the control unit such that the first operating condition is set when the desired delivery volume is not more than one half, one third or one fourth of the maximum delivery volume per stroke of the pump.

The invention furthermore relates to the use of a device as described herein for delivering a concentrate which is used for preparing dialysis fluids.

It is conceivable that the dialysis fluid is prepared in a dialysis machine, the device in accordance with the invention forming part of the dialysis machine. Alternatively, it is possible that the device is not part of the dialysis machine and that the concentrate or a dialysis fluid formed with the concentrate is delivered to the dialysis machine by means of the device.

The invention furthermore relates to a dialysis machine with a device as described herein. As stated above, the device of the invention is used in particular when a batch mode is employed in at least one operating condition. If the device is used in a dialysis machine, it turns out to be advantageous that in this case it is often not decisive that each batch contains the exact dosage. From the mixing point of the concentrate with the RO water up to the dialyzer, further components are present, such as the mixing chamber, balancing chamber, sterile filters and the dialyzer itself, in whose volumes the individual batches can be mixed. Moreover, minor conductivity variations are tolerable. It is decisive that on average an exact dosage is ensured over a certain number (e.g. 4) of batches, as is the case here.

The dialysis machine of the invention can include a concentrate container for receiving concentrate for preparing dialysis fluids, wherein on the suction side the displacement pump of the device is connected with the concentrate container. On the pressure side, there is preferably provided a mixing point in which the concentrate delivered is mixed with ultrapure water.

The invention furthermore relates to a method for delivering a fluid, preferably a medical fluid, in which the fluid is delivered by a pump designed as displacement pump, wherein during a suction stroke in a first operating mode the pump sucks in a volume exceeding the desired delivery volume and discharges portions of the volume sucked in by performing a plurality of partial delivery strokes in the form of partial volumes which are smaller than the volume sucked in.

Advantageous aspects of the method are subject-matter of the sub-claims. Particularly advantageously, the volume exceeding the desired delivery volume, which is sucked in during a suction stroke, corresponds to the maximum delivery volume per stroke of the pump or comes rather close to the same.

BRIEF DESCRIPTION OF THE DRAWINGS

Further details and advantages of the invention will be explained in detail with reference to an embodiment illustrated below, in which.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
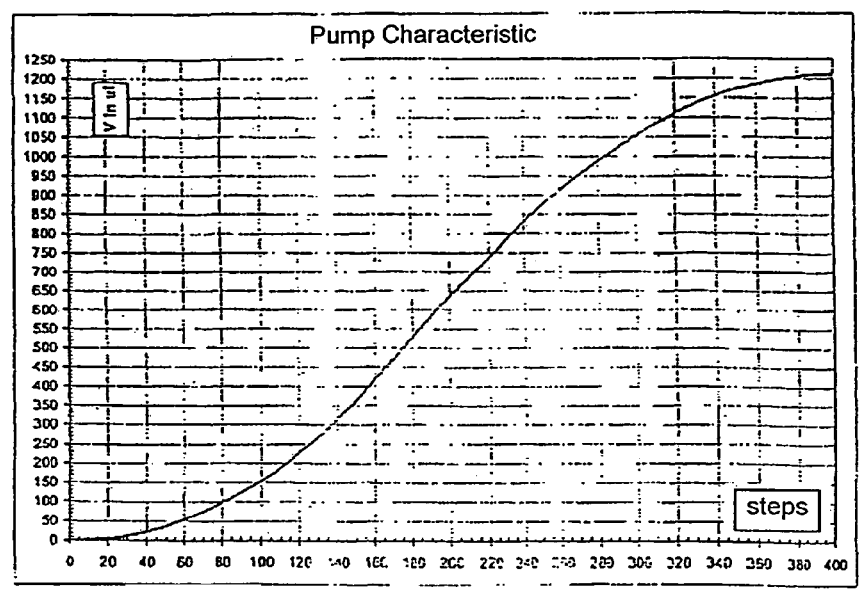
FIG. 1: shows a pump characteristic (delivery volume vs. number of steps) of a diaphragm pump.
Figure 2:
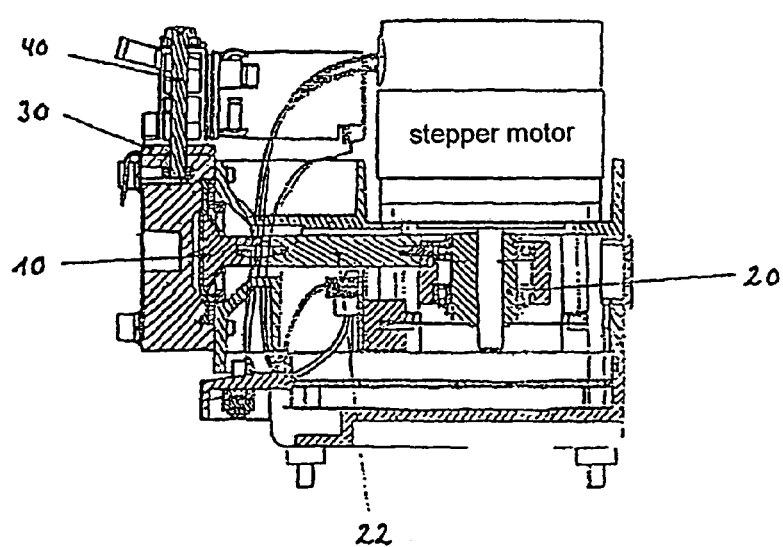
FIG. 2: shows a sectional view of a diaphragm pump.
Figure 3:
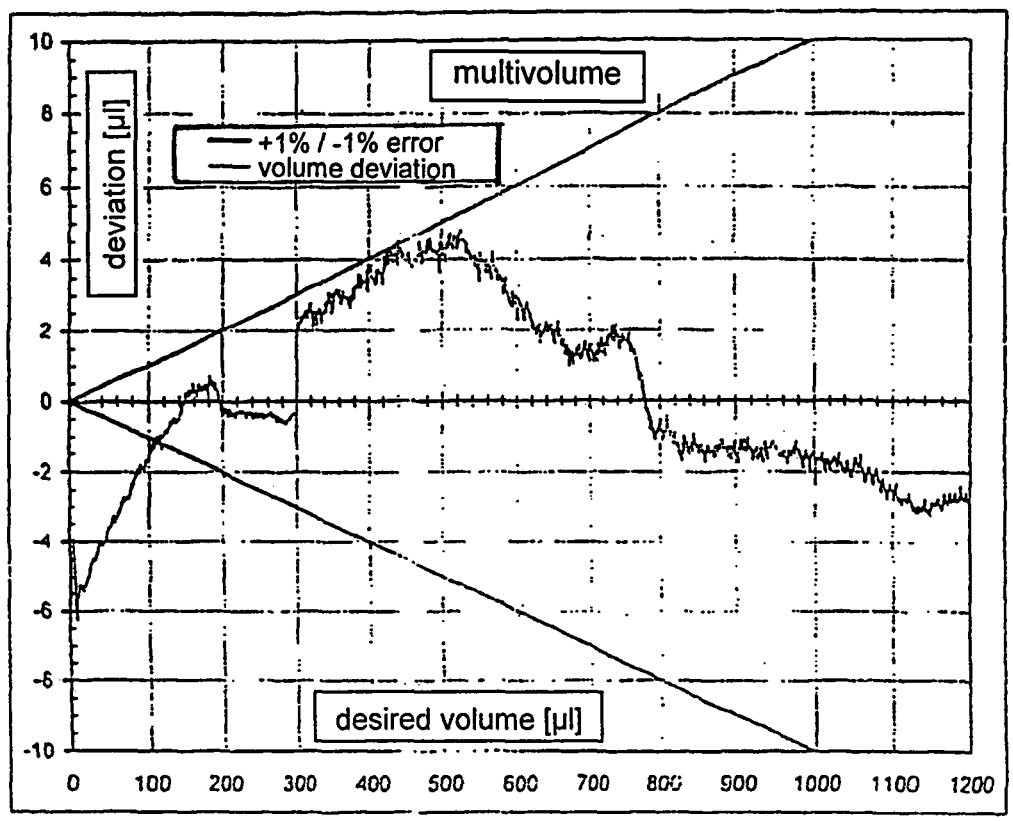
FIG. 3: shows an error characteristic by using the invention in the range between 200 µl and 300 µl.

FIG. 3 shows an error characteristic of a diaphragm pump which has a maximum delivery volume of 1200 µl per stroke. The course of the curve shows the deviation (in µl) of the volume delivered from the desired delivery volume in dependence on the desired delivery volume in μl. The straight error lines show the 1% deviation of the delivery volume from the desired delivery volume both for upward deviations (+1%) and downward deviations (−1%).

FIG. 3 reveals that in the case of larger desired delivery volumes the deviation of the actual value from the desired value is comparatively small, and thus the accuracy of the delivery is satisfactory.

FIG. 3 furthermore shows that an inaccurate delivery is obtained in particular in the range below 600 μl. The accuracies achieved here lie within the range of the +1% straight error line.

In the range below the desired delivery volume of 200 μl and above 300 μl, the volume sucked in was discharged in a single delivery stroke, which corresponds to the above-mentioned second operating condition of the pump. In the range between 200 μl and 300 μl, the pump was operated in the first operating condition, i.e. in this range the delivery principle of the invention was employed. The term "multivolume" indicated in FIG. 3 illustrates that for discharging the desired delivery volume in said range between 200 μl and 300 μl not this value, but a larger volume, for instance 1200 μl, was sucked in during a suction stroke, which then was discharged in the form of several partial volumes. For delivery in the range between 200 μl and 300 μl, four times the volume each was sucked in and delivered in four partial volumes.

What is of course also conceivable is a procedure in which in the range up to 300 μl a variable number of partial volumes is delivered in dependence on the desired delivery volume. It is conceivable that with desired delivery volumes up to 200 μl, six times the desired delivery volume is sucked in during a suction stroke and the volume sucked in is discharged in the form of six partial volumes. In the range between 201 μl and 240 μl it can be provided that five times the desired delivery volume is sucked in during a suction stroke and the volume sucked in is discharged in the form of five partial volumes. Between 241 μl and 300 μl it can be provided that four times the delivery volume is sucked in during a suction stroke and the volume sucked in is discharged in the form of four partial volumes.

Such gradation can also be provided beyond the range of 300 μl. It is conceivable that in the interval from 301 μl to 400 μl three times the volume is sucked in, and in the range from 401 μl to 600 μl twice the volume is sucked in and discharged in the form of three or two partial volumes, respectively. From 601 μl, it can be provided that the volume sucked in corresponds to the desired delivery volume and that the volume sucked in is discharged in one delivery stroke.

It is of course also conceivable that from 301 μl already, the volume sucked in corresponds to the desired delivery volume and that the volume sucked in is discharged in one delivery stroke.

Due to the comparatively large volume sucked in, the "multivolume range" between 200 μl and 300 μl provides an excellent delivery accuracy, as is revealed in FIG. 3 by the fact that the deviation between actual and desired value as plotted on the ordinate is very small. This provides the advantage that for delivering different volumes and hence also for delivering different concentrates a single pump can be used, a very good accuracy being achievable for the entire desired delivery range.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A dialysis machine, comprising:
a device that delivers a concentrate used for preparing a dialysis fluid in the dialysis machine, including
at least one pump configured as a displacement pump with a suction side and a pressure side; and
at least one control unit that controls operation of the pump, the pump being actuated by the control unit such that during a single suction stroke in a first operating condition,
on the suction side the pump sucks in a volume of the concentrate exceeding a desired delivery volume thereof so as to discharge the desired delivery volume, and
on the pressure side discharges portions of the volume sucked in by performing a plurality of partial delivery strokes as partial volumes which are smaller than the volume sucked in, the partial volumes each corresponding to the desired delivery volume.

2. The dialysis machine according to claim 1, wherein the pump is a diaphragm pump or piston pump.

3. The dialysis machine according to claim 1, wherein the pump is actuated by the control unit such that the volume sucked in during the suction stroke, which exceeds the desired delivery volume, lies in a range of from 0.5 to 1.0 of a maximum delivery volume per stroke of the pump.

4. The dialysis machine according to claim 1, wherein the pump is actuated by the control unit such that the volume sucked in during the suction stroke, which exceeds the desired delivery volume, corresponds to a maximum delivery volume per stroke of the pump.

5. The dialysis machine according to claim 1, wherein the pump is actuated by the control unit such the partial volumes discharged are identical or substantially identical.

6. The dialysis machine according to claim 1, wherein a ratio of the volume sucked in during the suction stroke to the partial volume discharged is about 10:1 or less.

7. The dialysis machine according to claim 1, wherein the pump is operated in a second operating condition, in which the volume sucked in during the suction stroke is not divided into the partial volumes.

8. The dialysis machine according to claim 7, wherein the pump is actuated by the control unit such that a choice of the operating condition by the control unit depends on the desired delivery volume.

9. The dialysis machine according to claim 7, wherein the pump is actuated by the control unit such that the first operating condition is set with smaller desired delivery volumes and the second operating condition is set with comparatively larger desired delivery volumes.

10. The dialysis machine according to claim 9, wherein the pump is actuated by the control unit such that the first operating condition is set when the desired delivery volume is not more than one half, one third, or one fourth of a maximum delivery volume per stroke of the pump.

11. The dialysis machine according to claim 1, wherein the device is separate from and independent of the dialysis machine.

12. The dialysis machine according to claim 1, further comprising a concentrate container for receiving the concentrate for preparing the dialysis fluid, the concentrate container being connected to a suction side of the pump.

13. A method of delivering a concentrate used for preparing a dialysis fluid in a dialysis machine, the method comprising the steps of:
delivering the concentrate with a device that includes at least one pump configured as a displacement pump with a suction side and a pressure side, and at least one control unit that controls operation of the pump, the step of delivering the concentrate including actuating the pump with the control unit such that during a single suction stroke in a first operating condition, on the suction side the pump sucks in a volume of the concentrate exceeding a desired delivery volume thereof so as to discharge the desired delivery volume, and on the pressure side discharges portions of the volume sucked in by performing a plurality of partial delivery strokes as partial volumes which are smaller than the volume sucked in, the partial volumes each corresponding to the desired delivery volume.

14. The method according to claim 13, wherein the volume taken in during the suction stroke, which exceeds the desired delivery volume, lies in a range of from 0.5 to 1.0 of a maximum delivery volume per stroke of the pump.

15. The method according to claim 13, wherein the volume taken in during the suction stroke, which exceeds the desired delivery volume, corresponds to a maximum delivery volume per stroke of the pump.

16. The method according to claim 13, wherein the partial volumes discharges are identical or substantially identical.

17. The method according to claim 13, wherein a ratio of the volume taken in during the suction stroke to the partial volume discharged is about 10:1 or less.

18. The method according to claim 13, wherein in a second operating condition the pump discharges the volume taken in during the suction stroke in one delivery stroke.

19. The method according to claim 18, wherein the operating condition of the pump is chosen based on the desired delivery volume.

20. The method according to claim 18, wherein with smaller desired delivery volumes the pump is operated in the first operating condition, and with comparatively larger desired delivery volumes, the pump is operated in a second operating condition.

21. The method according to claim 20, wherein the pump is operated in the first operating condition when the desired delivery volume is not more than one half, one third, or one fourth of a maximum delivery volume per stroke of the pump.

* * * * *

UNITED STATES PATENT AND TRADEMARK OFFICE
CERTIFICATE OF CORRECTION

PATENT NO.       : 8,430,833 B2                                                      Page 1 of 1
APPLICATION NO. : 11/921029
DATED            : April 30, 2013
INVENTOR(S)      : Gagel et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1042 days.

Signed and Sealed this
Eighth Day of September, 2015

Michelle K. Lee
*Director of the United States Patent and Trademark Office*